United States Patent [19]

Ariba et al.

[11] Patent Number: 5,226,070
[45] Date of Patent: Jul. 6, 1993

[54] MAT WITH LOW X-RAY ABSORPTION FOR X-RAY DIAGNOSIS

[75] Inventors: Masayuki Ariba, Ootawara; Kunitaka Kato, Utsunomiya; Tomiji Kamata, Tochigi, all of Japan

[73] Assignee: Kabushiki Kaisha Toshiba, Kawasaki, Japan

[21] Appl. No.: 881,313

[22] Filed: May 7, 1992

Related U.S. Application Data

[63] Continuation of Ser. No. 680,131, Apr. 3, 1991, abandoned.

[30] Foreign Application Priority Data

Apr. 3, 1990 [JP] Japan .................................. 2-88761

[51] Int. Cl.$^5$ .............................................. H05G 1/00
[52] U.S. Cl. ...................................... 378/208; 378/209
[58] Field of Search ................... 378/208, 209, 20, 68

[56] References Cited

U.S. PATENT DOCUMENTS

| 4,910,819 | 3/1990 | Brown | 378/209 |
| 4,926,457 | 5/1990 | Poehner et al. | 378/209 |
| 4,956,885 | 9/1990 | Alich et al. | 378/209 |
| 5,054,049 | 10/1991 | Manabe | 378/208 |

Primary Examiner—David P. Porta
Assistant Examiner—Kim-Kwok Chu
Attorney, Agent, or Firm—Oblon, Spivak, McClelland, Maier & Neustadt

[57] ABSTRACT

As mat is used in an X-ray diagnostic apparatus such as an X-ray CT apparatus. This mat comprises: a foaming plastic plate having at least major surfaces and edge portions, a biological body under medical examination being positioned above one of the major surfaces; and a waterproof sheet having an X-ray absorption coefficient higher than that of the foaming plastic plate, for covering the foaming plastic plate in such a manner that planes of the waterproof sheet at said edge portions of the foaming plastic plate are not positioned in parallel with parallel planes of the major surfaces.

2 Claims, 6 Drawing Sheets

MAT WITH LOW X-RAY ABSORPTION FOR X-RAY DIAGNOSIS

This application is a continuation of application Ser. No. 07/680,131, filed on Apr. 3, 1991, now abandoned.

BACKGROUND OF THE INVENTION

1. Field of the Invention

The present invention relates to a mat with low X-ray absorption used in an X-ray diagnostic apparatus, e.g., an X-ray CT (computerized tomographic) apparatus.

2. Description of the Related Art

In X-ray diagnostic apparatuses, various types of mats positioned on table tops have been utilized, on which a biological body under medical examination, for instance, a patient is mounted during medical examination, as represented in, e.g., U.S. Pat. No. 4,312,912 to Tamura, issued on Jan. 26, 1982.

In FIG. 1, there is shown a conventional mat 1, as a cross-sectional view, used in the X-ray diagnostic apparatus (not shown in detail).

More specifically, the mat 1 is employed for X-ray radiography or fluoroscopy equipped with an X-ray detecting means such as an image intensifier (not shown). The mat 1 is mounted on the table couch (not shown) made of wood, and the biological body (not shown) under X-ray examination is mounted on this mat 1.

As is known in the art, it is preferable to reduce the X-ray absorption coefficients of all materials or constructive members other than the object to be X-ray-examined, through which X-rays pass, as small as possible, and also to achieve uniform lower X-ray absorption amounts thereof. Accordingly, as a material for this mat 1, a foaming plastic plate 2 with an elastic characteristic having a thickness of approximately 30 mm, for instance, polyurethane foam is generally used because of a small X-ray absorption coefficient thereof.

In the X-ray radioscopy or fluoroscopy, a preselected chemical agent such as an X-ray contrast medium is utilized. To this end, the outer surfaces of the mat 1 is covered with a waterproof sheet 3 whose X-ray absorption coefficient is greater than that of the foaming plastic plate 2 with elastic characteristics, and two end portions of this waterproof sheet 3 are overlap-jointed with each other at both sides of the foaming plastic plate 2, as shown in FIG. 1.

In general, an X-ray projection direction of such an X-ray diagnostic apparatus is substantially perpendicular to a major plane of the mat 1 on which a biological body under medical examination is mounted. There are some possibilities that a diagnostic portion of the biological body under medical examination might exceed the edge portions of this mat 1, depending upon the body size. When such an exceeding diagnostic portion is imaged by the X-ray radiation, one X-ray beam "Xa" will pass through a portion "1a" near a center portion of the mat 1, having small aluminium equivalent for X-ray attenuation, e.g., 0.2 mm, whereas another X-ray beam "Xb" will pass through only a portion of the waterproof sheet 3 having a length of 30 mm at an end portion "1b" of this mat 1. Accordingly, since aluminium equivalent for X-ray attenuation of this end portion "1b" becomes larger than 1.5 mm, namely becomes 7 times higher than the aluminium equivalent of the above-described portion "1a", this end portion "1b" appears as a white line in a resultant X-ray image, which may give adverse influences to the X-ray diagnosis.

SUMMARY OF THE INVENTION

The present invention has been made in an attempt to solve the above-described problem, and therefore has an object to provide a novel mat used for an X-ray diagnosis which is free from averse influences given on X-ray images.

A mat used for an X-ray diagnosis apparatus (20) comprising:

a foaming plastic plate (12:42) having at least major surfaces and edge portions (15:45), a biological body (P) under medical examination being positioned above one of said major surfaces; and, a waterproof sheet (13:33) having an X-ray absorption coefficient higher than that of said foaming plastic plate (12:32), for covering said foaming plastic plate (12:32) in such a manner that planes of said waterproof sheet at said edge portions (15:35) of the foaming plastic plate (12:32) are not positioned in parallel with parallel planes of said major surfaces.

BRIEF DESCRIPTION OF THE DRAWINGS

The present invention will now be described further by way of an example only and with reference to the accompanying drawing, in which.

DETAILED DESCRIPTION OF THE PREFERRED EMBODIMENT

BASIC IDEA

As previously explained, the X-ray absorption coefficient of the waterproof sheet 3 is considerably greater than that of the foaming plastic plate 2.

As a consequence, in a mat according to the present invention, a total length of a waterproof sheet through which an X-ray beam passes may be minimized as much as possible. To this end, for instance, a plane or planes of this waterproof sheet at an end portion of this mat is so arranged as not to be positioned in parallel with an X-ray beam path.

APPLICATION OF FIRST MAT TO X-RAY RADIOGRAPHIC APPARATUS

Figure 1:
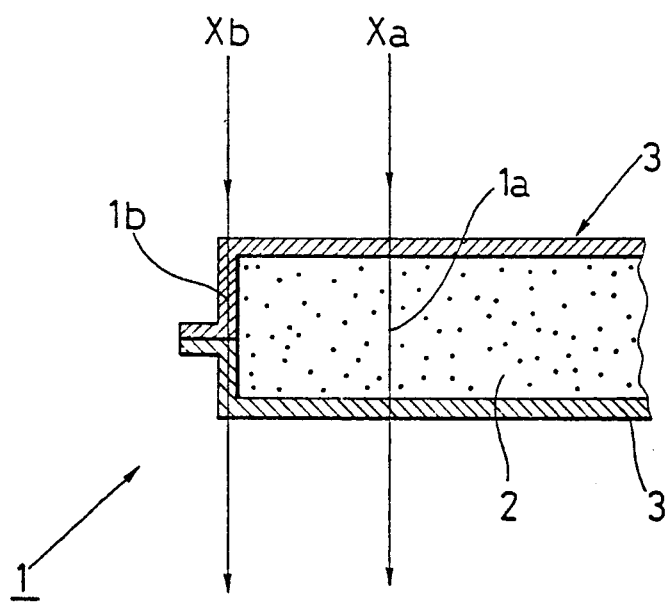
FIG. 1 is a cross-sectional view of a major portion of the conventional mat 1 for the X-ray diagnosis.
Figure 2:
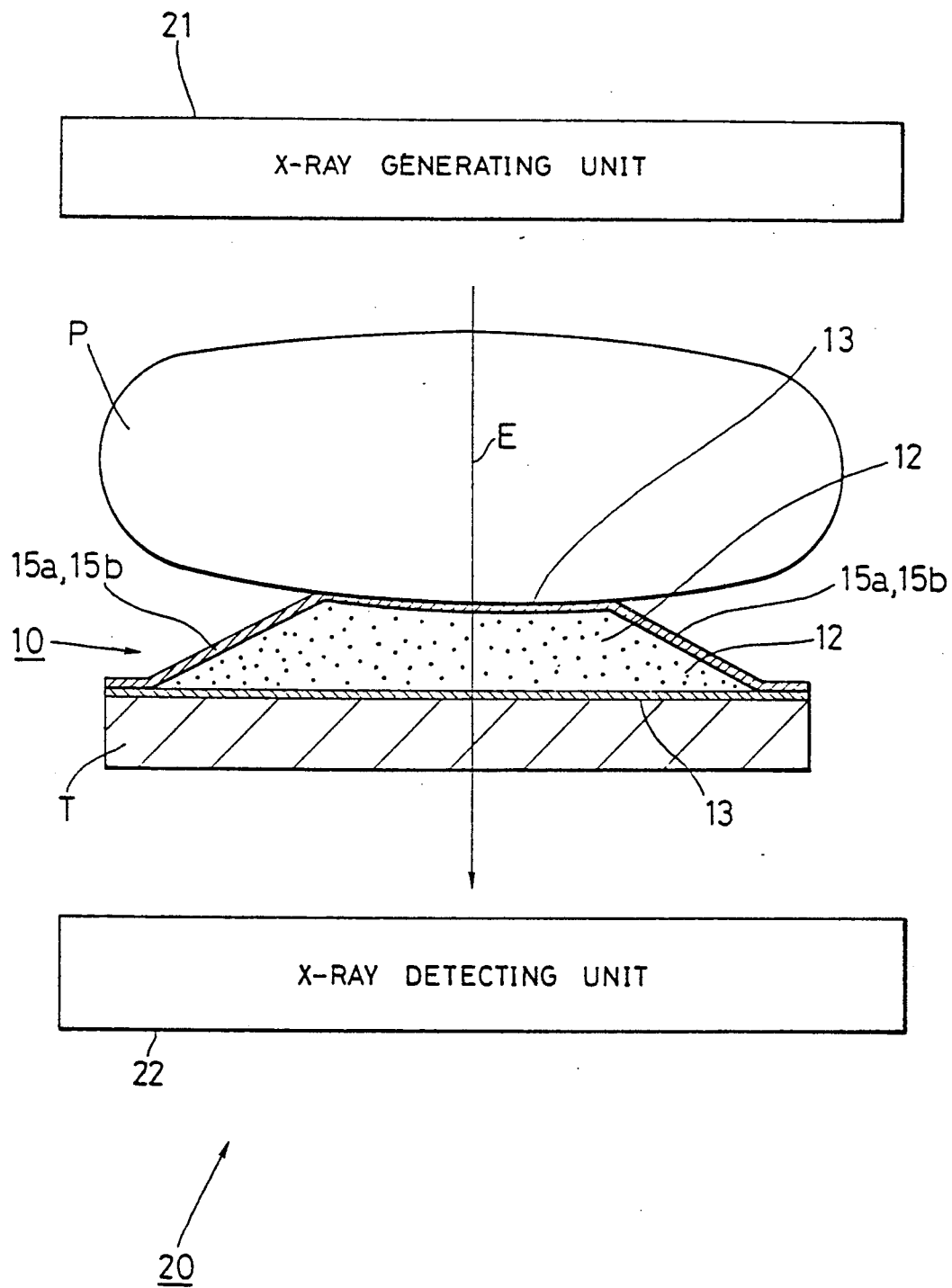
FIG. 2 pictorically represents a mat 10 according to a first preferred embodiment of the present invention, which is applied to an X-ray radiographic apparatus 20.

FIG. 2 pictorically illustrates an X-ray radiographic apparatus 20 to which a mat 10 used for X-ray diagnostic purposes according to the present invention has been applied.

In the X-ray radiographic apparatus 20, there are provided an X-ray generating unit 21, e.g., an X-ray tube (not shown in detail) for generating X-ray beams; a table top "T" for supporting a biological body "P" under medical examination such as a patient; and an X-ray detecting unit 22, e.g., an image intensifier (not shown in detail) for detecting the X-ray beams which has passed through the biological body "P". These constructive units 21, "T" and 22 are arranged in a specific positional relationship as represented in FIG. 2.

The mat 10 according to the first preferred embodiment is positioned on the table top "T" and the biological body "P" is mounted on this mat 10.

STRUCTURE OF FIRST MAT

Figure 3:
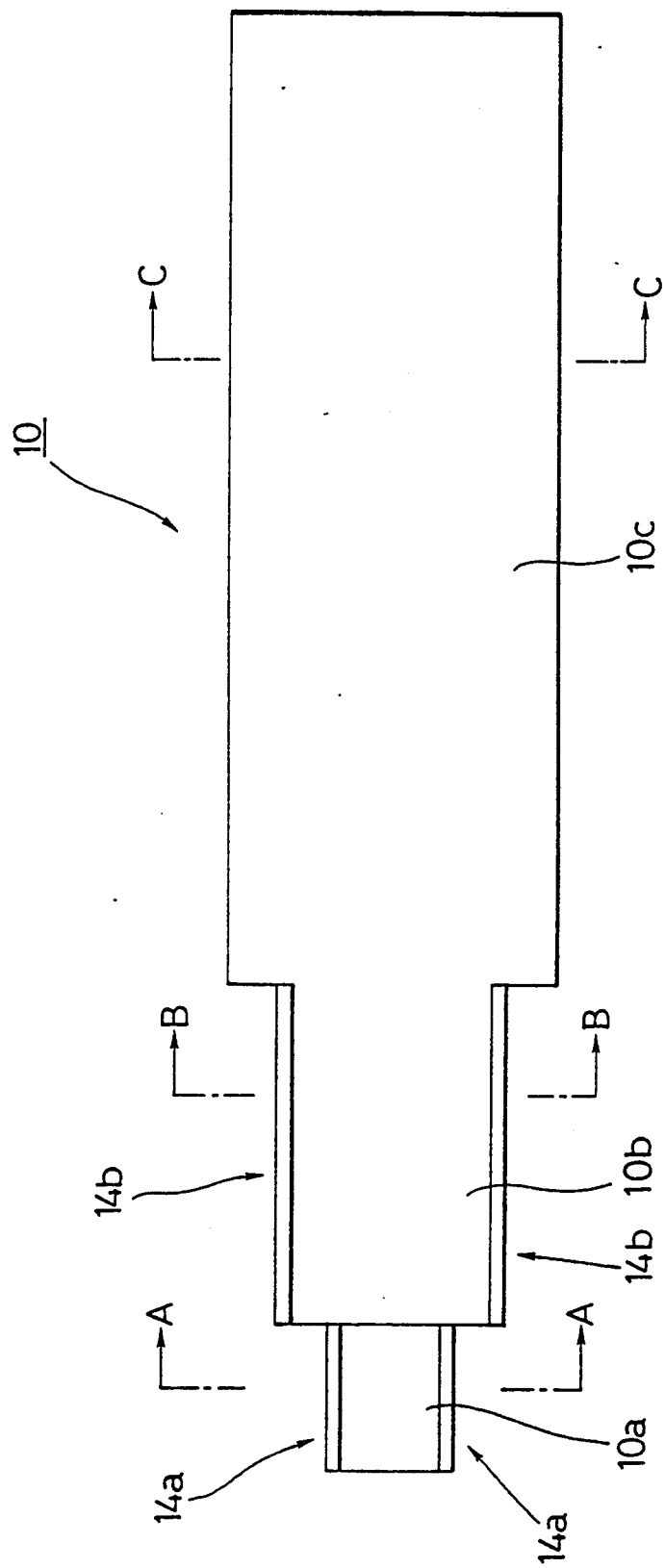
FIG. 3 is a plan view of the first mat 10, the cross-sectional view of which is represented in FIG. 2.
Figure 4:
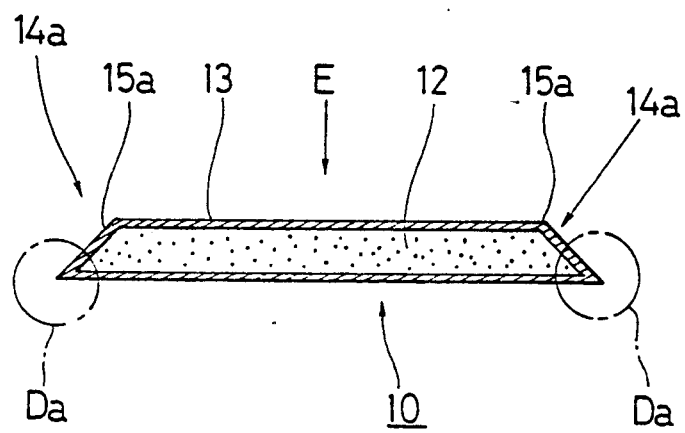
FIG. 4 is a cross-sectional view of the mat 10, taken along a line A—A in FIG. 3.
Figure 5:
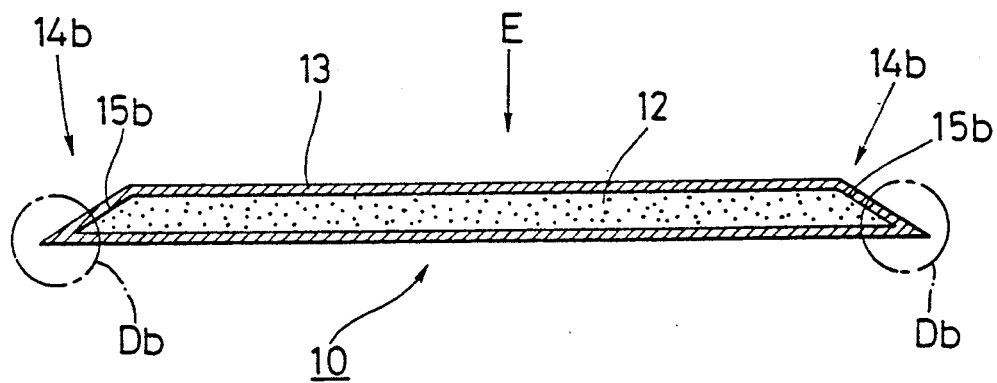
FIG. 5 is a cross-sectional view of the mat 10, taken along a line B—B in FIG. 3.

FIG. 3 is a plan view of the entire first mat 10; FIG. 4 is a cross-sectional view of the first mat 10, taken along a line A—A shown in FIG. 3; FIG. 5 is a cross-sectional view of the first mat 10, taken along a line B—B shown in FIG. 3; and also FIG. 6 is a cross-sectional view of the first mat 10, taken along a line C—C shown in FIG. 3.

The first mat 10 is so constructed that a foaming plastic plate 12 with elasticity having a thickness of approximately 30 mm and made of polyurethane foam or the like, is covered with a waterproof sheet 13 having a thickness of about 0.3 mm and made of a synthetic leather or the like, and end portions of the waterproof sheet 13 positioned at edge portions "Da" to "Dc" of the foaming plastic plate 12 are overlap-jointed with each other. As represented in FIG. 3, the first mat 10 is mainly constructed of a head accepting part 10a, a chest accepting part 10b and a waist accepting portion 10c.

As known in the X-ray diagnostic field, it is preferably to detect X-ray beams under such a condition that the X-ray detecting unit 22 must be approached to both the head portion of the biological body "P" and the chest portion thereof as closely as possible, since both these head and chest portions require precise X-ray inspection. There are some cases that the X-ray radiography is carried out in a direction perpendicular to the X-ray beam traveling direction "E". To this end, widths of the head accepting part 10a and also the chest accepting part 10b are designed to be substantially equal to a standard size of a biological body "P" under medical examination, due to the focal length of the X-ray diagnostic apparatus and also no disturbance during the rotations of the X-ray source and X-ray detector.

Figure 6:
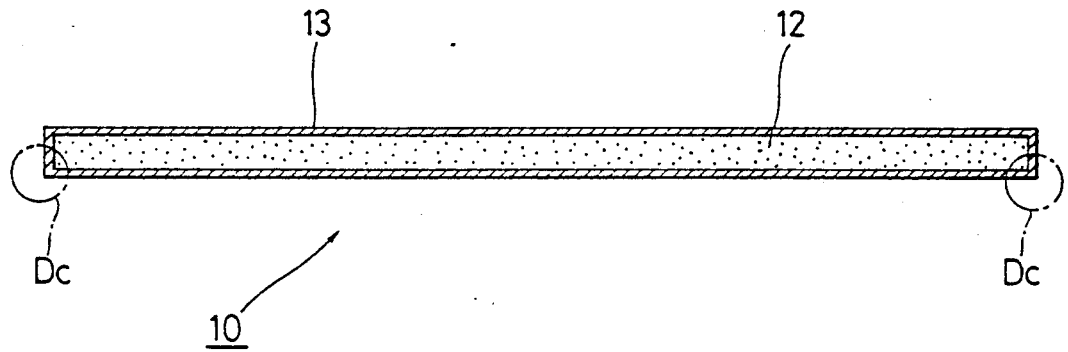
FIG. 6 is a cross-sectional view of the mat 10, taken along a line C—C in FIG. 3.

On the other hand, since no precise X-ray inspection is required for the leg portion of the biological body, a width of the waist accepting part 10c of the first mat 10 is designed to be wider than a standard width of the biological body (see FIG. 6). Both edge portions 14a and 14b of the head accepting unit 10a and chest accepting unit 10b have inclined planes 15a and 15b as shown in FIGS. 4 and 5, respectively. In accordance with the first preferred embodiment, planes of the waterproof sheet 13 at these edge portions 14a an 14b are not positioned parallel to the X-ray transmission (traveling) direction "E" so as to reduce attenuation of the X-ray beams which pass through the relevant planes of the waterproof sheet 13. As a result, aluminium equivalent for X-ray attenuation of the overall first mat 10 may be made small and may be uniformed along the X-ray transmission direction "E", whereby no adverse influence caused by the unwanted X-ray attenuation occurring in the first mat 10 may be given to the resultant X-ray images.

The above-described first mat 10 has the following particular advantages. First, even when either the head portion or the chest portion of the biological body "P" exceeds the edge portion of the waterproof sheet 13, namely the inclined portion 15a or 15b, since all planes of the waterproof sheet 13 are not positioned in parallel with the X-ray transmission direction "E", the X-ray images having a better image quality may be obtained. Moreover, even if the X-ray imaging is performed at the inclined planes 15a and 15b of the edge portions 14a and 14b of the first mat 10 within such a range that the X-ray projection direction is not parallel to the X-ray transmission direction "E", the X-ray images with better qualities may be obtained.

STRUCTURE OF SECOND MAT

Figure 7:
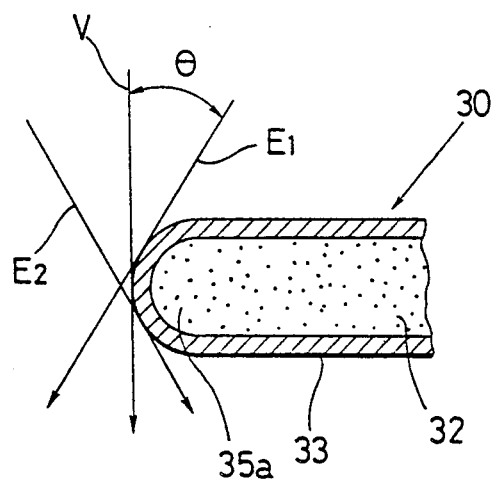
FIG. 7 is a cross-sectional view of a major portion of another mat 30 according to a second preferred embodiment of the present invention; and, FIG. 8 is a cross-sectional view of a major portion of a further mat 40 according to a third preferred embodiment of the present invention.

Referring now to FIG. 7, a structure of a mat 30 according to a second preferred embodiment of the present invention will be described.

The second mat 30 has semicircular-shaped edge portions "35a" and "35b (not shown)". Even when the inclined angle "$\theta$" becomes great (for instance, 80°), a total thickness of a waterproof sheet 33 through which X-ray beams pass, does not have a large value along the X-ray transmission direction "E". The inclined angle "$\theta$" is defined by one X-ray transmission line "$E_1$" and a vertical line "V". Accordingly, the second mat 30 has a similar advantage to that of the above-described first mat 10.

STRUCTURE OF THIRD MAT

Figure 8:
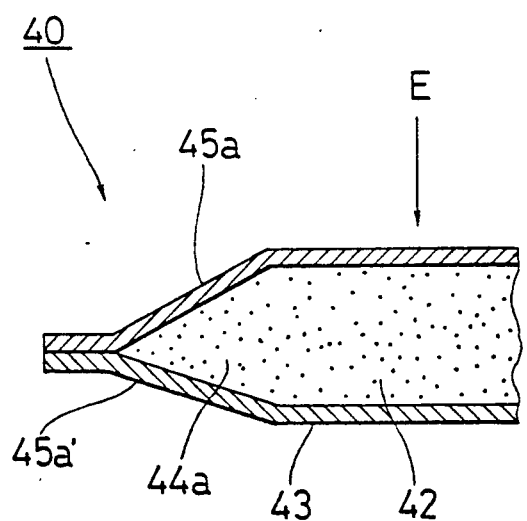

FIG. 8 is a cross-sectional view of a major edge portion of a mat 40 according to a third preferred embodiment of the present invention.

As apparent from FIG. 8, two inclined planes 45a and 45a' are formed on each of two end portions "44a" and "44b (not shown)". An overlap-jointed portion of a waterproof sheet 43 is therefore positioned at an intermediate portion of each of the end portions "44a" and "44b" along a thickness direction of a foaming plastic plate 42 with elasticity. Similarly, the third mat 40 has the substantially same particular advantage as that of the first mat 10.

As apparent from the foregoing descriptions, the present invention is not limited to the above-described preferred embodiments, but may be readily modified without departing from the technical spirit and scope of the present invention. For instance, any shapes of end portions of the mat may be employed unless adverse influences are given to the image qualities of the resultant X-ray image. Also, the mats according to the present invention may be utilized in not only the above-described X-ray radiography, but also any types of X-ray CT (computerized tomography) apparatus. Moreover, materials and thickness of the mats according to the present invention may be freely employed other than those of the first to third mats 10, 30 and 40.

While the present invention has been described above, since the planes of the edge portions of the waterproof sheet are not positioned parallel to the X-ray traveling direction, the attenuation occurring when the X-ray beam passes through the equivalent thickness of the waterproof sheet may be considerably reduced, as compared with the conventional mat. As a consequence, X-ray images having better image quantities may be obtained.

What is claimed is:

1. A mat set between a patient and a couch used in an X-ray diagnostic apparatus, comprising:
   a foaming plastic plate having at least substantially parallel major surfaces and substantially semicircular-shaped edge portions; and
   a waterproof sheet having an X-ray absorption coefficient higher than that of said foaming plastic plate for covering said substantially semicircular-shaped edge portions of the foaming plastic plate, whereby edge portions of said waterproof sheet have substantially semi-circular shapes similar to that of said substantially semicircular-shaped edge portions.

2. A mat as claimed in claim 1, wherein a thickness of said major surfaces of the foaming plastic plate is selected to be approximately 30 mm, whereas that of said waterproof sheet is selected to be approximately 0.3 mm.

* * * * *